US009638699B2

(12) United States Patent
Figtree et al.

(10) Patent No.: US 9,638,699 B2
(45) Date of Patent: May 2, 2017

(54) BIOMARKERS OF OXIDATIVE STRESS

(71) Applicants: Northern Sydney Local Health District, St. Leonards, NSW (AU); The University of Sydney, Sydney, NSW (AU)

(72) Inventors: Gemma Alexandra Figtree, Waverton (AU); Chia-Chi Liu, Caringbah (AU); Natasha Alexandria Sarah Fry, Manly (AU); Keyvan Karimi Galougahi, St. Leonards (AU)

(73) Assignees: The University of Sydney, Sydney (AU); Northern Sydney Local Health District, St. Leonards (AU)

( * ) Notice: Subject to any disclaimer, the term of this patent is extended or adjusted under 35 U.S.C. 154(b) by 0 days.

(21) Appl. No.: 14/069,913

(22) Filed: Nov. 1, 2013

(65) Prior Publication Data

US 2015/0024413 A1    Jan. 22, 2015

(30) Foreign Application Priority Data

Jul. 18, 2013    (AU) ................................ 2013902669

(51) Int. Cl.
  *G01N 33/68*    (2006.01)
(52) U.S. Cl.
  CPC ..... *G01N 33/6872* (2013.01); *G01N 2800/32* (2013.01); *G01N 2800/325* (2013.01); *G01N 2800/7009* (2013.01)
(58) Field of Classification Search
  CPC ........... G01N 33/6872; G01N 2800/32; G01N 2800/325; G01N 2800/7009
  See application file for complete search history.

(56) References Cited

U.S. PATENT DOCUMENTS

| | | | |
|---|---|---|---|
| 6,953,666 B1 | 10/2005 | Kinkade, Jr. et al. | |
| 7,482,174 B2 | 1/2009 | Kiefer et al. | |
| 7,915,001 B2 | 3/2011 | Reginster et al. | |
| 8,030,010 B2 | 10/2011 | Des Rosiers et al. | |
| 8,030,011 B2 | 10/2011 | Kiernan et al. | |
| 8,137,978 B2 | 3/2012 | Ford et al. | |
| 8,137,979 B2 | 3/2012 | Combes et al. | |
| 8,293,481 B2 | 10/2012 | Brozovich et al. | |
| 8,317,997 B2 | 11/2012 | Bar-Or et al. | |
| 8,338,110 B2 | 12/2012 | Hazen et al. | |
| 8,969,300 B2 * | 3/2015 | Rasmussen | 514/15.1 |
| 2008/0014595 A1 | 1/2008 | Janssen-Heininger et al. | |

FOREIGN PATENT DOCUMENTS

WO        00/28072        5/2000

OTHER PUBLICATIONS

Abbasi et al. "Peroxiredoxin 4, A Novel Circulating Biomarker for Oxidative Stress and the Risk of Incident Cardiovascular Disease and All-Cause Mortality" J Am Heart Assoc. 2012;1:e002956 doi: 10.1161/JAHA.112.002956.
Bibert et al. "FXYD Proteins Reverse Inhibition of the Na+-K+ Pump Mediated by Glutathionylation of Its β1 Subunit" JBC Papers in Press. Published on Mar. 30, 2011 as Manuscript M110.184101.
Bionutrics News Release dated Mar. 6, 2000 entitled "Bionutrics secures exclusive rights to patented oxidative stress diagnostic kit".
Bundgaard et al. "⊕3 Adrenergic Stimulation of the Cardiac Na—K Pump by Reversal of an Inhibitory Oxidative Modification" Circulation. 2010;122:2699-2708.
Dalle-Donne et al. "Biomarkers of Oxidative Damage in Human Disease" Clinical Chemistry 52:4 601-623 (2006).
Figtree et al. "Reversible Oxidative Modification: A Key Mechanism of Na—K Pump Regulation" Circ Res. 2009;105:185-193.
Figtree et al. "Oxidative regulation of the Na—K pump in the cardiovascular system" Free Radical Biology and Medicine 53 (2012) 2263-2268.
Heart Research Australia "Understanding and regulating a key heart molecule." Website article accessed Nov. 7, 2011.
Kim, Hyeon Chang "Clinical Utility of Novel Biomarkers in the Prediction of Coronary Heart Disease" Korean Circ J 2012;42:223-228.
Lee et al. "Evaluating Oxidative Stress in Human Cardiovascular Disease: Methodological Aspects and Considerations" Current Medicinal Chemistry, 2012, 19, 2504-2520.
Liu et al "Glutathionylation of Erythrocyte Na—K Pump in Heart Failure: A Novel Biomarker That Reflects a Key Oxidative Change in the Heart" Abstract for American Heart Association Nov. 2012, 1 page.
Liu et al "Glutathionylation of Erythrocyte Na—K Pump in Heart Failure: A Novel Biomarker That Reflects a Key Oxidative Change in the Heart" Poster for American Heart Association Nov. 2012, 1 page.
McDonnell et al. "Cardiac biomarkers and the case for point-of-care testing" Clinical Biochemistry 42 (2009) 549-561.
Palmieri et al. "Oxidative stress tests: overview on reliability and use Part II" European Review for Medical and Pharmacological Sciences 2007; 11: 383-399.
Schnabel et al. "Oxidative Stress in Cardiovascular Disease Successful Translation From Bench to Bedside?" Circulation. 2007;116:1338-1340.
Vassiliadis et al. "Novel Cardiac-Specific Biomarkers and the Cardiovascular Continuum" Biomarker Insights 2012:7 45-57.
Wang et al. "Prognostic Utility of Novel Biomarkers of Cardiovascular Stress: The Framingham Heart Study" http://dx.doi.org/10.1161/Circulationaha.112.129437 Circulation. 2012; Circulationaha.112.129437; Originally published Aug. 20, 2012.

\* cited by examiner

*Primary Examiner* — Ruixiang Li
(74) *Attorney, Agent, or Firm* — Casimir Jones, SC

(57) ABSTRACT

The present invention relates to a method for detecting cardiovascular oxidative stress in an individual, comprising detecting in a blood sample from the individual modification of a cysteine at position 45 of the β1-subunit of the human erythrocyte ATP-dependent $Na^+K^+$ pump protein or of an equivalent cysteine in a homolog or variant thereof. The invention further relates to a kit for detecting cardiovascular oxidative stress in an individual, the kit comprising at least one agent for detecting the presence of a modification in a cysteine at position 45 of the β1-subunit of the human erythrocyte ATP-dependent $Na^+K^+$ pump protein or of an equivalent cysteine in a homolog or variant thereof, wherein said modification is a result of oxidation.

10 Claims, 4 Drawing Sheets

A. Structure of Na⁺-K⁺ pump and $\beta_1$ subunit C45 shown to be susceptible to glutathionylation B. Mutation of $\beta_1$ subunit Cys45 ($\alpha1\beta1CW$) abolishes ONOO-induced glutathionylation and inhibition of the Na⁺-K⁺ pump

A. Detection of eβ1-GSS in rabbits

B. ELISA assay for eβ1-GSS

C. eβ1-GSS in HF vs sham rabbits

D. Correlation of eβ1-GSS with β1 subunit glutathionylation in cardiac myocytes

A. Detection of eβ1-GSS in humans

C. Na-K pump activity in erythrocytes from HF patients vs. control

B. eβ1-GSS HF patients vs. control

SEQUENCE LISTING

<160> NUMBER OF SEQ ID NOS: 3

<210> SEQ ID NO 1
<211> LENGTH: 1023
<212> TYPE: PRT
<213> ORGANISM: Homo sapiens

<400> SEQUENCE: 1

| | | | | | | | | | | | | | | |
|---|---|---|---|---|---|---|---|---|---|---|---|---|---|---|
| Met | Gly | Lys | Gly | Val | Gly | Arg | Asp | Lys | Tyr | Glu | Pro | Ala | Ala | Val | Ser |
| 1 | | | | 5 | | | | | 10 | | | | | 15 | |

| Glu | Gln | Gly | Asp | Lys | Lys | Gly | Lys | Lys | Lys | Asp | Arg | Asp | Met |
|---|---|---|---|---|---|---|---|---|---|---|---|---|---|
| | | | 20 | | | | | 25 | | | | | 30 |

| Asp | Glu | Leu | Lys | Lys | Glu | Val | Ser | Met | Asp | Asp | His | Lys | Leu | Ser | Leu |
|---|---|---|---|---|---|---|---|---|---|---|---|---|---|---|---|
| | | | | 35 | | | | | 40 | | | | | 45 | |

| Asp | Glu | Leu | His | Arg | Lys | Tyr | Gly | Thr | Asp | Leu | Ser | Arg | Gly | Leu | Thr |
|---|---|---|---|---|---|---|---|---|---|---|---|---|---|---|---|
| | | | 50 | | | | | 55 | | | | | 60 | | |

| Ser | Ala | Arg | Ala | Ala | Glu | Ile | Leu | Ala | Arg | Asp | Gly | Pro | Asn | Ala | Leu |
|---|---|---|---|---|---|---|---|---|---|---|---|---|---|---|---|
| 65 | | | | | 70 | | | | | 75 | | | | | 80 |

| Thr | Pro | Pro | Pro | Thr | Thr | Pro | Glu | Trp | Ile | Lys | Phe | Cys | Arg | Gln | Leu |
|---|---|---|---|---|---|---|---|---|---|---|---|---|---|---|---|
| | | | | 85 | | | | | 90 | | | | | 95 | |

| Phe | Gly | Gly | Phe | Ser | Met | Leu | Leu | Trp | Ile | Gly | Ala | Ile | Leu | Cys | Phe |
|---|---|---|---|---|---|---|---|---|---|---|---|---|---|---|---|
| | | | | 100 | | | | | 105 | | | | | 110 | |

| Leu | Ala | Tyr | Ser | Ile | Gln | Ala | Ala | Thr | Glu | Glu | Glu | Pro | Gln | Asn | Asp |
|---|---|---|---|---|---|---|---|---|---|---|---|---|---|---|---|
| | | | | 115 | | | | | 120 | | | | | 125 | |

| Asn | Leu | Tyr | Leu | Gly | Val | Val | Leu | Ser | Ala | Val | Val | Ile | Ile | Thr | Gly |
|---|---|---|---|---|---|---|---|---|---|---|---|---|---|---|---|
| | | | 130 | | | | | 135 | | | | | 140 | | |

| Cys | Phe | Ser | Tyr | Tyr | Gln | Glu | Ala | Lys | Ser | Ser | Lys | Ile | Met | Glu | Ser |
|---|---|---|---|---|---|---|---|---|---|---|---|---|---|---|---|
| 145 | | | | | 150 | | | | | 155 | | | | | 160 |

| Phe | Lys | Asn | Met | Val | Pro | Gln | Gln | Ala | Leu | Val | Ile | Arg | Asn | Gly | Glu |
|---|---|---|---|---|---|---|---|---|---|---|---|---|---|---|---|
| | | | | 165 | | | | | 170 | | | | | 175 | |

| Lys | Met | Ser | Ile | Asn | Ala | Glu | Glu | Val | Val | Val | Gly | Asp | Leu | Val | Glu |
|---|---|---|---|---|---|---|---|---|---|---|---|---|---|---|---|
| | | | 180 | | | | | 185 | | | | | 190 | | |

| Val | Lys | Gly | Gly | Asp | Arg | Ile | Pro | Ala | Asp | Leu | Arg | Ile | Ile | Ser | Ala |
|---|---|---|---|---|---|---|---|---|---|---|---|---|---|---|---|
| | | | 195 | | | | | 200 | | | | | 205 | | |

| Asn | Gly | Cys | Lys | Val | Asp | Asn | Ser | Ser | Leu | Thr | Gly | Glu | Ser | Glu | Pro |
|---|---|---|---|---|---|---|---|---|---|---|---|---|---|---|---|
| | 210 | | | | | 215 | | | | | 220 | | | | |

| Gln | Thr | Arg | Ser | Pro | Asp | Phe | Thr | Asn | Glu | Asn | Pro | Leu | Glu | Thr | Arg |
|---|---|---|---|---|---|---|---|---|---|---|---|---|---|---|---|
| 225 | | | | | 230 | | | | | 235 | | | | | 240 |

| Asn | Ile | Ala | Phe | Phe | Ser | Thr | Asn | Cys | Val | Glu | Gly | Thr | Ala | Arg | Gly |
|---|---|---|---|---|---|---|---|---|---|---|---|---|---|---|---|
| | | | | 245 | | | | | 250 | | | | | 255 | |

| Ile | Val | Val | Tyr | Thr | Gly | Asp | Arg | Thr | Val | Met | Gly | Arg | Ile | Ala | Thr |
|---|---|---|---|---|---|---|---|---|---|---|---|---|---|---|---|
| | | | 260 | | | | | 265 | | | | | 270 | | |

| Leu | Ala | Ser | Gly | Leu | Glu | Gly | Gly | Gln | Thr | Pro | Ile | Ala | Ala | Glu | Ile |
|---|---|---|---|---|---|---|---|---|---|---|---|---|---|---|---|
| | | 275 | | | | | 280 | | | | | 285 | | | |

| Glu | His | Phe | Ile | His | Ile | Ile | Thr | Gly | Val | Ala | Val | Phe | Leu | Gly | Val |
|---|---|---|---|---|---|---|---|---|---|---|---|---|---|---|---|
| | | 290 | | | | | 295 | | | | | 300 | | | |

| Ser | Phe | Phe | Ile | Leu | Ser | Leu | Ile | Leu | Glu | Tyr | Thr | Trp | Leu | Glu | Ala |
|---|---|---|---|---|---|---|---|---|---|---|---|---|---|---|---|
| 305 | | | | | 310 | | | | | 315 | | | | | 320 |

| Val | Ile | Phe | Leu | Ile | Gly | Ile | Ile | Val | Ala | Asn | Val | Pro | Glu | Gly | Leu |
|---|---|---|---|---|---|---|---|---|---|---|---|---|---|---|---|
| | | | | 325 | | | | | 330 | | | | | 335 | |

| Leu | Ala | Thr | Val | Thr | Val | Cys | Leu | Thr | Leu | Thr | Ala | Lys | Arg | Met | Ala |
|---|---|---|---|---|---|---|---|---|---|---|---|---|---|---|---|
| | | | 340 | | | | | 345 | | | | | 350 | | |

| Arg | Lys | Asn | Cys | Leu | Val | Lys | Asn | Leu | Glu | Ala | Val | Glu | Thr | Leu | Gly |
|---|---|---|---|---|---|---|---|---|---|---|---|---|---|---|---|
| | | 355 | | | | | 360 | | | | | 365 | | | |

-continued

```
Ser Thr Ser Thr Ile Cys Ser Asp Lys Thr Gly Thr Leu Thr Gln Asn
    370                 375                 380

Arg Met Thr Val Ala His Met Trp Phe Asp Asn Gln Ile His Glu Ala
385                 390                 395                 400

Asp Thr Thr Glu Asn Gln Ser Gly Val Ser Phe Asp Lys Thr Ser Ala
                    405                 410                 415

Thr Trp Leu Ala Leu Ser Arg Ile Ala Gly Leu Cys Asn Arg Ala Val
            420                 425                 430

Phe Gln Ala Asn Gln Glu Asn Leu Pro Ile Leu Lys Arg Ala Val Ala
                435                 440                 445

Gly Asp Ala Ser Glu Ser Ala Leu Leu Lys Cys Ile Glu Leu Cys Cys
450                 455                 460

Gly Ser Val Lys Glu Met Arg Glu Arg Tyr Ala Lys Ile Val Glu Ile
465                 470                 475                 480

Pro Phe Asn Ser Thr Asn Lys Tyr Gln Leu Ser Ile His Lys Asn Pro
                485                 490                 495

Asn Thr Ser Glu Pro Gln His Leu Leu Val Met Lys Gly Ala Pro Glu
                500                 505                 510

Arg Ile Leu Asp Arg Cys Ser Ser Ile Leu Leu His Gly Lys Glu Gln
            515                 520                 525

Pro Leu Asp Glu Glu Leu Lys Asp Ala Phe Gln Asn Ala Tyr Leu Glu
530                 535                 540

Leu Gly Gly Leu Gly Glu Arg Val Leu Gly Phe Cys His Leu Phe Leu
545                 550                 555                 560

Pro Asp Glu Gln Phe Pro Glu Gly Phe Gln Phe Asp Thr Asp Asp Val
                565                 570                 575

Asn Phe Pro Ile Asp Asn Leu Cys Phe Val Gly Leu Ile Ser Met Ile
                580                 585                 590

Asp Pro Pro Arg Ala Ala Val Pro Asp Ala Val Gly Lys Cys Arg Ser
            595                 600                 605

Ala Gly Ile Lys Val Ile Met Val Thr Gly Asp His Pro Ile Thr Ala
610                 615                 620

Lys Ala Ile Ala Lys Gly Val Gly Ile Ile Ser Glu Gly Asn Glu Thr
625                 630                 635                 640

Val Glu Asp Ile Ala Ala Arg Leu Asn Ile Pro Val Ser Gln Val Asn
                645                 650                 655

Pro Arg Asp Ala Lys Ala Cys Val Val His Gly Ser Asp Leu Lys Asp
            660                 665                 670

Met Thr Ser Glu Gln Leu Asp Asp Ile Leu Lys Tyr His Thr Glu Ile
            675                 680                 685

Val Phe Ala Arg Thr Ser Pro Gln Gln Lys Leu Ile Ile Val Glu Gly
690                 695                 700

Cys Gln Arg Gln Gly Ala Ile Val Ala Val Thr Gly Asp Gly Val Asn
705                 710                 715                 720

Asp Ser Pro Ala Leu Lys Lys Ala Asp Ile Gly Val Ala Met Gly Ile
                725                 730                 735

Ala Gly Ser Asp Val Ser Lys Gln Ala Ala Asp Met Ile Leu Leu Asp
            740                 745                 750

Asp Asn Phe Ala Ser Ile Val Thr Gly Val Glu Glu Gly Arg Leu Ile
            755                 760                 765

Phe Asp Asn Leu Lys Lys Ser Ile Ala Tyr Thr Leu Thr Ser Asn Ile
770                 775                 780

Pro Glu Ile Thr Pro Phe Leu Ile Phe Ile Ile Ala Asn Ile Pro Leu
```

```
                785                 790                 795                 800
Pro Leu Gly Thr Val Thr Ile Leu Cys Ile Asp Leu Gly Thr Asp Met
                    805                 810                 815

Val Pro Ala Ile Ser Leu Ala Tyr Glu Gln Ala Glu Ser Asp Ile Met
                    820                 825                 830

Lys Arg Gln Pro Arg Asn Pro Thr Asp Lys Leu Val Asn Glu Arg
                    835                 840                 845

Leu Ile Ser Met Ala Tyr Gly Gln Ile Gly Met Ile Gln Ala Leu Gly
    850                 855                 860

Gly Phe Phe Thr Tyr Phe Val Ile Leu Ala Glu Asn Gly Phe Leu Pro
865                 870                 875                 880

Ile His Leu Leu Gly Leu Arg Val Asp Trp Asp Arg Trp Ile Asn
                    885                 890                 895

Asp Val Glu Asp Ser Tyr Gly Gln Trp Thr Tyr Gln Arg Lys
                    900                 905                 910

Ile Val Glu Phe Thr Cys His Thr Ala Phe Phe Val Ser Ile Val Val
                    915                 920                 925

Val Gln Trp Ala Asp Leu Val Ile Cys Lys Thr Arg Arg Asn Ser Val
    930                 935                 940

Phe Gln Gln Gly Met Lys Asn Lys Ile Leu Ile Phe Gly Leu Phe Glu
945                 950                 955                 960

Glu Thr Ala Leu Ala Ala Phe Leu Ser Tyr Cys Pro Gly Met Gly Val
                    965                 970                 975

Ala Leu Arg Met Tyr Pro Leu Lys Pro Thr Trp Trp Phe Cys Ala Phe
                    980                 985                 990

Pro Tyr Ser Leu Leu Ile Phe Val  Tyr Asp Glu Val Arg  Lys Leu Ile
                    995                 1000                1005

Ile Arg  Arg Arg Pro Gly Gly  Trp Val Glu Lys Glu  Thr Tyr Tyr
                    1010                1015                1020

<210> SEQ ID NO 2
<211> LENGTH: 303
<212> TYPE: PRT
<213> ORGANISM: Homo sapiens

<400> SEQUENCE: 2

Met Ala Arg Gly Lys Ala Lys Glu Glu Gly Ser Trp Lys Lys Phe Ile
1                   5                   10                  15

Trp Asn Ser Glu Lys Lys Glu Phe Leu Gly Arg Thr Gly Gly Ser Trp
                    20                  25                  30

Phe Lys Ile Leu Leu Phe Tyr Val Ile Phe Tyr Gly Cys Leu Ala Gly
                35                  40                  45

Ile Phe Ile Gly Thr Ile Gln Val Met Leu Leu Thr Ile Ser Glu Phe
    50                  55                  60

Lys Pro Thr Tyr Gln Asp Arg Val Ala Pro Gly Leu Thr Gln Ile
65                  70                  75                  80

Pro Gln Ile Gln Lys Thr Glu Ile Ser Phe Arg Pro Asn Asp Pro Lys
                    85                  90                  95

Ser Tyr Glu Ala Tyr Val Leu Asn Ile Val Arg Phe Leu Glu Lys Tyr
                    100                 105                 110

Lys Asp Ser Ala Gln Arg Asp Asp Met Ile Phe Glu Asp Cys Gly Asp
                    115                 120                 125

Val Pro Ser Glu Pro Lys Glu Arg Gly Asp Phe Asn His Glu Arg Gly
    130                 135                 140
```

```
Glu Arg Lys Val Cys Arg Phe Lys Leu Glu Trp Leu Gly Asn Cys Ser
145                 150                 155                 160

Gly Leu Asn Asp Glu Thr Tyr Gly Tyr Lys Glu Gly Lys Pro Cys Ile
            165                 170                 175

Ile Ile Lys Leu Asn Arg Val Leu Gly Phe Lys Pro Lys Pro Pro Lys
            180                 185                 190

Asn Glu Ser Leu Glu Thr Tyr Pro Val Met Lys Tyr Asn Pro Asn Val
            195                 200                 205

Leu Pro Val Gln Cys Thr Gly Lys Arg Asp Glu Asp Lys Asp Lys Val
            210                 215                 220

Gly Asn Val Glu Tyr Phe Gly Leu Gly Asn Ser Pro Gly Phe Pro Leu
225                 230                 235                 240

Gln Tyr Tyr Pro Tyr Tyr Gly Lys Leu Leu Gln Pro Lys Tyr Leu Gln
                245                 250                 255

Pro Leu Leu Ala Val Gln Phe Thr Asn Leu Thr Met Asp Thr Glu Ile
            260                 265                 270

Arg Ile Glu Cys Lys Ala Tyr Gly Glu Asn Ile Gly Tyr Ser Glu Lys
            275                 280                 285

Asp Arg Phe Gln Gly Arg Phe Asp Val Lys Ile Glu Val Lys Ser
290                 295                 300

<210> SEQ ID NO 3
<211> LENGTH: 66
<212> TYPE: PRT
<213> ORGANISM: Homo sapiens

<400> SEQUENCE: 3

Met Thr Gly Leu Ser Met Asp Gly Gly Ser Pro Lys Gly Asp Val
1               5                   10                  15

Asp Pro Phe Tyr Tyr Asp Tyr Glu Thr Val Arg Asn Gly Gly Leu Ile
            20                  25                  30

Phe Ala Gly Leu Ala Phe Ile Val Gly Leu Leu Ile Leu Leu Ser Arg
            35                  40                  45

Arg Phe Arg Cys Gly Gly Asn Lys Lys Arg Arg Gln Ile Asn Glu Asp
        50                  55                  60

Glu Pro
65
```

BIOMARKERS OF OXIDATIVE STRESS

CROSS-REFERENCE TO RELATED APPLICATIONS

The present application claims priority to pending Australian Patent Application No. 2013902669, filed Jul. 18, 2013, the contents of which are incorporated by reference in its entirety.

TECHNICAL FIELD

The present invention relates to methods for assessing oxidative stress in the circulation for the purposes of prognosis and diagnosis of cardiovascular disease (CVD) and impending or existing heart failure. The invention also relates to biomarkers and kits for measuring the severity of ongoing oxidative stress relevant to progression of CVD and/or of heart failure. The invention further relates to methods for monitoring recovery of an individual from circulatory oxidative stress and methods for assessing the efficacy of an agent for treatment of cardiovascular disease states associated with elevated oxidative stress.

BACKGROUND

ATP-dependent $Na^+$—$K^+$ pump is a transmembrane enzyme, found in almost all cells of higher organisms, that is responsible for the active transport of sodium ions out of cells in exchange for extracellular potassium ions against their respective electrochemical gradients. A key function of the $Na^+$—$K^+$ pump is to generate the gradients required to maintain the resting membrane potential of electrically excitable cells. These gradients have important additional roles in driving the transmembrane transport of other ions and organic compounds, such as calcium and glucose, and in regulating cell volume.

$Na^+$—$K^+$ pump dysfunction is important in heart failure, cardiac ischaemia and vascular dysfunction. The pump maintains low intracellular $Na^+$ levels and in turn drives $Ca^{2+}$ efflux via the $Na^+$—$Ca^{2+}$ exchanger. Inhibition of the cardiac $Na^+$—$K^+$ pump results in abnormally elevated intracellular $Na^+$ levels that disturb $Ca^{2+}$ balance, leading to impaired contractility and arrhythmias in the case of heart failure and cardiac ischaemia, and altered vascular tone. Approaches to reverse $Na^+$—$K^+$ pump inhibition may be a useful therapeutic strategy.

Reactive oxygen species (ROS) are generated as a by-product of normal metabolic reactions in the body and subsequently can cause extensive damage to proteins, lipids, and DNA.

Oxidative stress plays a large role in cardiovascular pathophysiology, including atherosclerosis, hypertension, cardiomyopathy, and chronic heart failure in humans. Strenuous physical exercise also results in oxidative damage in the circulatory system as a result of elevated ROS levels during exercise. Oxidative stress also has a role in the pathophysiology of diabetes, renal failure, neurological and inflammatory disorders, ageing, cancer and hypertension. However, biomarkers of oxidative stress have generally not been particularly successful due to the technical difficulties in measuring oxidative stress in the circulation, or at the organ level, in vivo.

A number of biochemical markers of CVD, such as troponin I and T, are now commonly used in clinics to measure myocardial damage. However, the majority of the existing markers are useful only in the end stages of the disease where few successful intervention options exist.

The prevalence and impact of cardiac dysfunction continues to escalate. Identification of those at risk of heart failure, or those with mild, but undiagnosed heart failure will assist in earlier and more cost-effective application of therapies—prior to the development of disabling symptoms and costly hospitalization. Furthermore, identification of negative prognostic factors in individuals with heart failure or CVD may allow physicians to target aggressive therapeutic options. Since a large number of individuals experience a transient underlying developing pathology long before the signs or symptoms of CVD become apparent, there is a requirement for new markers that can describe the early tissue-specific, matrix remodelling process which ultimately leads to disease, and to link these markers to their intervention point along the cardiovascular continuum. Given the role oxidative stress plays in cardiovascular pathophysiology, an object of the present invention is to provide a biomarker that reflects oxidative stress. Such a marker would then be able to act as an "integrator" for many of the conventional risk factors for cardiovascular disease that are united by their mediation via ROS, as well as many other "difficult-to-define" risk factors.

SUMMARY

The present invention is based, at least in part, on the determination that oxidation of a cysteine residue at position 45 of the erythrocyte ATP-dependent $Na^+$—$K^+$ pump $\beta 1$ subunit correlates with the severity of ongoing CVD and impending heart failure, or even existing (but undiagnosed) heart failure in an individual. In embodiments, the invention relates to methods for the prognosis of CVD or heart failure. In embodiments, the methods of the invention may be used to assess individuals with CVD or heart failure by determining which individuals are more likely to develop serious complications, such as defined by the need for hospital admission or the need for life-support therapy.

The invention has application in healthcare, such as in the early management of cardiovascular disease states characterized by high levels of oxidative stress. Early identification of individuals at risk of cardiovascular disease, such as coronary artery disease, or heart failure, will allow the introduction of life-saving prophylactic interventions to at-risk individuals. For example, the inventors envisage that in individuals presenting to an emergency department with suspected heart failure or at-risk signs of impending heart failure can assist the clinician to predict whether an individual can be safely discharged home, or may need admission to hospital or even interventional treatment. Similarly, the inventors envisage that in individuals who are admitted to the hospital, an identified level of circulatory oxidative damage can assist the clinician to predict whether an individual will deteriorate further (ICU admission) or recover. The inventors envisage that detected levels of circulatory oxidative damage may also be used to assist a clinician or therapist in the ongoing monitoring of an individual, for example after medicinal therapy or other care associated with the treatment of the individual's condition.

According to an embodiment of the invention, there is provided a method for detecting cardiovascular oxidative stress in an individual, said method comprising detecting in a blood sample from said individual modification of a cysteine 45 of the $\beta 1$-subunit of the human erythrocyte ATP-dependent $Na^+$—$K^+$ pump protein or of an equivalent cysteine in a non-human homologue or variant thereof.

According to an embodiment, the modification comprises glutathionylation of said cysteine 45 or equivalent thereof.

According to an aspect, the method is for determining the prognosis of an individual with risk factors for CVD, wherein the level of modification of said cysteine detected in the individual's blood is indicative of the severity of cardiovascular oxidative stress in said individual.

According to another aspect, the method is for determining whether an individual is at risk of heart failure or has undiagnosed heart failure, wherein the level of modification of said cysteine detected in the individual's blood is indicative of the risk of heart failure in said individual or indicative of whether the individual is suffering heart failure.

According to a further aspect, the method is for monitoring the recovery of an individual, or for monitoring the effectiveness of treatment of an individual suffering from cardiovascular oxidative stress, wherein a change in the level of modification of said cysteine detected in the individual's blood is indicative of the individual's recovery or the effectiveness of the treatment.

Said method may be for monitoring recovery of said individual from impending or ongoing cardiovascular disease, such as coronary artery disease/events, or heart failure. Alternatively, said method may be for monitoring recovery of said individual from strenuous physical exercise.

According to a further aspect, the method is for assessing the efficacy of an agent for treatment or prevention of cardiovascular disease states characterized by elevated oxidative stress in an individual. The method may comprise administering the agent to an individual having cardiovascular oxidative stress and detecting the level of a modified cysteine 45 of the $\beta_1$-subunit of the human erythrocyte ATP-dependent $Na^+K^+$ pump protein or of an equivalent cysteine in a homologue or a variant thereof in a blood sample from said individual and comparing said detected level of modified cysteine to a level of modified cysteine detected for said individual at an earlier time point, wherein a decrease in the level of modified cysteine detected in said individual is indicative of an agent capable of treating impending or existing heart failure. Alternatively, the method may comprise administering the agent to an individual, and detecting the level of a modified cysteine at position 45 of the $\beta_1$-subunit of the human erythrocyte ATP-dependent $Na^+K^+$ pump protein or of an equivalent cysteine in a homologue or a variant thereof in a blood sample from said individual before and after exposing said individual to a cardiovascular oxidative challenge, wherein no change or a minor change in the level of modified cysteine detected in said individual is indicative of an agent effective for preventing cardiovascular oxidative stress. Said agent may be for treatment of impending or existing ongoing cardiovascular disease, such as coronary artery disease/events, heart failure, or for treatment of circulatory oxidative damage resulting from strenuous exercise.

According to another embodiment of the invention, there is provided a kit for detecting cardiovascular oxidative stress in an individual, the kit comprising at least one agent for detecting the presence of a modification of a cysteine at position 45 of the β1-subunit of the human erythrocyte ATP-dependent $Na^+K^+$ pump protein or of an equivalent cysteine in a homologue or variant thereof, wherein said modification is a result of oxidation.

ABBREVIATIONS

The abbreviation CVD is used herein for cardiovascular disease.

The abbreviation CHD is used herein for coronary heart disease.

The abbreviation $e\beta 1$ is used herein to identify the $\beta_1$ subunit of the erythrocyte ATP-dependent $Na^+$—$K^+$ pump protein. Similarly, the term $e\beta 1$-GSS is used herein to identify the glutathionylated $\beta_1$ subunit of the erythrocyte ATP-dependent $Na^+$—$K^+$ pump protein.

DEFINITIONS

As used in this application, the singular form "a", "an" and "the" include plural references unless the context clearly dictates otherwise.

Unless the context requires otherwise or it is specifically stated to the contrary, integers, steps, or elements of the invention recited herein as singular integers; steps or elements clearly encompass both singular and plural forms of the recited integers, steps or elements.

The term "at least one" when used in the context of a group of selectable elements includes any and all members of the group individually selected and includes any combination of the members of the group. Similarly, the term "at least two" when used in the context of a group of selectable elements includes any selection of two or more members of the group in any combination.

As used herein, the term "comprising" means "including." Variations of the word "comprising", such as "comprise" and "comprises," have correspondingly varied meanings. Thus, for example, a polynucleotide "comprising" a sequence encoding a protein may consist exclusively of that sequence or may include one or more additional sequences. Similarly a method "comprising" one or more stated activities may consist exclusively of those activities or may include one or more additional activities. Similarly a kit "comprising" one or more stated components may consist exclusively of those components or may include one or more additional components.

As used herein, the terms "antibody" and "antibodies" are used in their broadest meaning and include IgG (including IgG1, IgG2, IgG3, and IgG4), IgA (including IgA1 and IgA2), IgD, IgE, or IgM, and IgY, whole antibodies, including single-chain whole antibodies, and antigen-binding fragments thereof. Antigen-binding antibody fragments include, but are not limited to, Fab, Fab' and F(ab')2, Fd, single-chain Fvs (scFv), single-chain antibodies, disulfide-linked Fvs (sdFv) and fragments comprising either a VL or VH domain. The antibodies may be from any animal origin. Antigen-binding antibody fragments, including single-chain antibodies, may comprise the variable region(s) alone or in combination with the entire or partial of the following: hinge region, CH1, CH2, and CH3 domains. Also included are any combinations of variable region(s) and hinge region, CH1, CH2, and CH3 domains. Antibodies may be monoclonal, polyclonal, chimeric, multispecific, humanized, and human monoclonal and polyclonal antibodies that specifically bind the biological molecule.

As used herein, the term "detection" may refer to qualitative as well as quantitative detection, and may include observation, measurement, and/or quantification as well as detection, and these terms may be used interchangeably throughout. Variations of the word "detection", such as "detecting", "detect" and "detects" have correspondingly similar scopes.

As used herein, the terms "polypeptide" and "protein" are used interchangeably and are taken to have the same meaning.

As used herein, the term "homologue" in the context of proteins means proteins having substantially the same functions and similar properties in different species, and which, within at least regions, share at least 50% amino acid identity. Such homologous proteins may share, over their entire amino acid sequences, at least about 30% amino acid identity, at least about 40% amino acid identity, at least about 50% amino acid identity, at least about 60% amino acid identity, at least about 70% amino acid identity, at least about 80% amino acid identity, at least about 90% amino acid identity or at least about 95% identity. Similarly, homologues of nucleic acid molecules are nucleic acid molecules that encode proteins having substantially the same functions and similar properties in different species, wherein the encoded proteins share, within at least regions, at least 50% amino acid identity (such nucleic acid homologues may share significantly less than 50% identity due to degeneracy in the genetic code, and differences in preferred codon usage amongst different genuses and species), and may share at least about 30% amino acid identity, at least about 40% amino acid identity, at least about 50% amino acid identity, at least about 60% amino acid identity, at least about 70% amino acid identity, at least about 80% amino acid identity, at least about 90% amino acid identity or at least about 95% identity over the whole encoded amino acid sequences. Furthermore, as used herein, the term "variant" in the context of a peptide or protein includes peptides or proteins differing from the subject peptide or protein by virtue of addition, deletion, or substitution of one or more amino acids compared to the subject peptide or protein, such as may arise from, for example, mutation or natural variation.

As used herein, the term "kit" refers to any delivery system for delivering materials. In the context of the detection assays and methods described herein, such delivery systems include systems that allow for the storage, transport, or delivery of reaction reagents (for example labels, reference samples, supporting material, etc. in the appropriate containers) and/or supporting materials (for example, buffers, written instructions for performing the assay, etc.) from one location to another. For example, kits include one or more enclosures, such as boxes, containing the relevant reaction reagents and/or supporting materials.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of this application.

For the purposes of description all documents referred to herein are incorporated by reference in their entirety unless otherwise stated.

DETAILED DESCRIPTION

Figure 1:
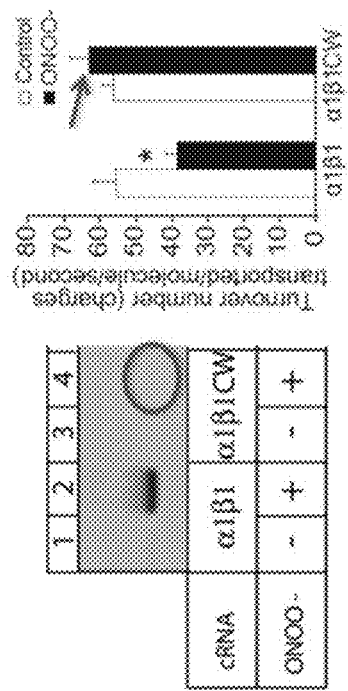
FIG. 1: A shows the structure of pig kidney $Na^+$—$K^+$-ATPase showing the position of the $\beta1$ subunit C45 (red circle). $\alpha$- $\beta$- and $\gamma$ (a.k.a. FXYD2) subunits are shown as blue, wheat and red. A schematic illustration of mixed disulfide bond between glutathione and reactive cysteine on candidate protein is shown. B illustrates results that show that mutation of the 01 subunit Cys45 (equivalent to Cys46 in *Xenopus*) to tryptophan ($\alpha1\beta1CW$) abolishes $ONOO^-$-induced glutathionylation (circle) and inhibition (arrow) of the $Na^+$—$K^+$ pump in *Xenopus* oocytes.
Figure 1:
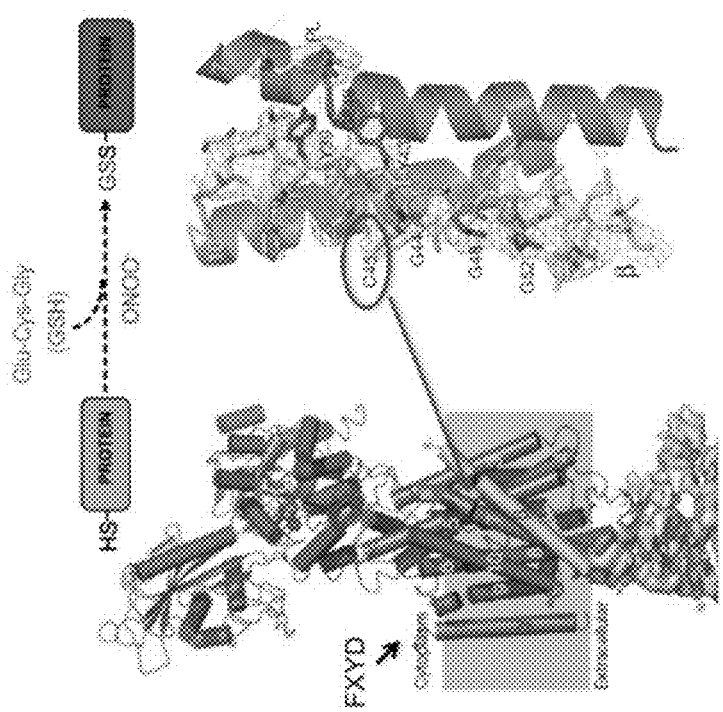

CVD is the biggest killer of both men and women world-wide, and large numbers of individuals have risk factors for CVD. Applying a simple test that has ability to risk stratify these individuals may allow for reduction in morbidity and mortality through targeting of aggressive treatment protocols.

Many risk prediction models have been developed in an effort to assist clinicians in risk assessment and the prevention of coronary heart disease (CHD). Yet, it is unclear whether the existing CHD prediction tools can improve clinical performance, and recently, there has been a lot of effort made to improve the accuracy of the prediction models. A large number of novel biomarkers have been identified as being associated with cardiovascular risk, and studied with the goal of improving the accuracy and clinical utility of CHD risk prediction. Yet, controversy still remains with regard to the utility of novel biomarkers in CHD risk assessment, and in finding the best statistical methods to assess the incremental value of the biomarkers. Even with the multiple biomarker approach, a reliable set of biomarkers that improves CHD risk evaluation sufficiently is yet to be identified. Additionally, the clinical utility of newer biomarkers in CHD prediction can be population-specific.

Oxidative stress is also a key feature in atherogenesis, since reactive oxygen species (ROS) are involved in all stages of the disease, from endothelial dysfunction to atheromatic plaque formation and rupture. One review of Oxidative stress measurement in atherosclerosis states that "measurement of circulating biomarkers of oxidative stress is challenging, since circulation usually behaves as a separate compartment to the individual structures of the vascular wall. However, measurement of stable products released by the reaction of ROS and vascular/circulating molecular structures is a particularly popular approach.

Oxidative inhibition of the cardiac $Na^+$—$K^+$ pump has been previously identified by the inventors as a key mechanism of its regulation. Oxidative inhibition is increased in response to neurohormonal abnormalities and oxidative stress characteristic of heart failure and other CVD states. This occurs because of formation of a stable mixed disulphide bond between glutathione and Cys45 of the pump's $\beta1$ subunit—a reaction known as glutathionylation. The bond is the causal factor in the relationship between this glutathionylation of the $\beta1$ subunit, leading to oxidant-induced pump inhibition. However, the bond is reversible, leading to potential for therapies to alter oxidative inhibition of the pump and thus regulation of Na—K pump induced impaired contractility and arrhythmias in CVD.

Thus glutathionylation of the cardiac myocyte $Na^+$—$K^+$ pump's β1 subunit (mβ1-GSS) can be a good prognostic marker that reflects both hormonal dysregulation and oxidative stress in the heart which in turn lead to Na—K dysfunction and thus cellular (myocyte) dysfunctional regulation of $Na^+$ and $Ca^{2+}$ across the cell membrane (also in other diseases with cells that are not myocytes). However, analysing glutathionylation of the cardiac myocyte $Na^+$—$K^+$ pump's β1 subunit requires invasive sampling techniques, specifically a biopsy of the heart, which is not a feasible option for use as a biomarker in humans.

In the course of the present studies it has been surprisingly found that the level of oxidation of C45 of the β1 subunit of circulating erythrocyte $Na^+$—$K^+$ pump (eβ1-GSS) closely correlates with the level of oxidation of C45 of the β1 subunit of the cardiac myocyte $Na^+$—$K^+$ pump. Erythrocyte β1-GSS is thus a circulating marker that is easily measured (for example, via a single blood sample) and reflects a physiologically significant consequence of ROS in the microcirculation.

The premise that eβ1-GSS will have prognostic value in individuals at risk of, or diagnosed with HF is supported by: (i) the close correlation between circulating erythrocyte β1-GSS and cardiac β1-GSS; (ii) the direct impact of oxidative $Na^+$—$K^+$ pump inhibition on cardiac myocyte physiology; and (iii) erythrocyte β1-GSS's reflection of the oxidative stress and neurohormonal abnormalities of heart failure. Furthermore, because eβ1-GSS reflects the underlying abnormalities driving cardiac dysfunction, it has potential advantages in detecting early heart failure. In contrast NT-proBNP, currently the strongest available marker and which requires ventricular stretch for release, becomes elevated only after established left ventricular dilatation in asymptomatic relatives of individuals with dilated cardiomyopathy.

The present invention is therefore based, at least in part, on the identification by the inventors that oxidation of the cysteine at position 45 in the human erythrocyte $Na^+$—$K^+$ pump's β1 subunit correlates strongly with cardiovascular oxidative stress, and the severity of cardiovascular pathophysiology in an individual, such as ongoing cardiovascular disease, such as coronary artery disease/events, or impending or existing heart failure. The invention may be used to assess individuals suffering from ongoing CVD or even impending heart failure, and determining appropriate treatment or management of such individuals. The invention may also be used to assess an individual for undiagnosed CVD or even undiagnosed heart failure. The invention also has application in monitoring a number of other physiological conditions resulting in cardiovascular oxidative stress, typically of an inflammatory nature. Non-limiting examples of such applications may include monitoring recovery of individuals, such as athletes, after strenuous physical exercise, or monitoring ongoing cardiovascular oxidative stress resulting from conditions such as diabetes (especially type 2 diabetes), dyslipidemia and metabolic syndrome.

Oxidation of the cysteine at position 45 in the human erythrocyte $Na^+$—$K^+$ pump's β1 subunit should therefore be a clinically useful prognostic biomarker in individuals with risk factors for CVD, including heart failure and myocardial infarction. This will allow targeted/individualized treatment, eg. with titration of medications that antagonize the neurohormonal dysregulation (eg. angiotensin II receptor antagonists; angiotensin converting enzyme inhibitors, beta-blockers), as well as the ability to measure the responsiveness of individuals to specific treatments aimed at reducing oxidative stress and neurohormonal abnormalities. This biomarker has the potential to be applied to everyone with risk factors for CVD, and also to be applied to determination and/or monitoring of circulatory oxidative damage in a broader sense, such as after strenuous exercise.

In one aspect of the invention there is therefore provided a method for detecting cardiovascular oxidative stress in an individual, said method comprising detecting in a blood sample from said individual modification of a cysteine at position 45 of the β1-subunit of the human erythrocyte ATP-dependent $Na^+K^+$ pump protein or of an equivalent cysteine in a homologue or variant thereof. According to an embodiment, the modification comprises glutathionylation of said cysteine 45 or equivalent thereof.

In another aspect of the invention there is provided use of an agent capable of detecting a modification of a cysteine, such as glutathionylation, at position 45 of the β1-subunit of the human erythrocyte ATP-dependent $Na^+K^+$ pump protein or of an equivalent cysteine in a homologue or variant thereof in a blood sample for the manufacture of a diagnostic for detecting cardiovascular oxidative stress in an individual.

In another aspect of the invention there is provided an agent capable of detecting a modification of a cysteine at position 45 of the β1-subunit of the human erythrocyte ATP-dependent $Na^+K^+$ pump protein or of an equivalent cysteine in a homologue or variant thereof in a blood sample for use in a method of detecting cardiovascular oxidative stress in an individual.

A method of the invention may be for determining the prognosis of an individual with risk factors for CVD, wherein the level of modification of said cysteine in the individual's blood is indicative of the severity of cardiovascular oxidative stress in the individual. The individual may be treated, or the individual's existing treatment regime may be altered as necessary, according to the severity of oxidative stress detected.

Alternatively, a method of the invention may be for determining whether an individual is at risk of heart failure or has undiagnosed heart failure, wherein the level of modification of said cysteine detected in the individual's blood is indicative of the risk of heart failure in the individual or indicative of whether the individual is suffering heart failure. Prophylactic or interventional therapy may be administered to the individual on determination of imminent or existing heart failure.

A method of the invention may be for monitoring the recovery of an individual, or for monitoring the effectiveness of treatment of an individual suffering from cardiovascular oxidative stress, wherein a change in the level of modification of said cysteine in the individual's blood compared to a previously detected level is indicative of the individual's recovery or the effectiveness of the treatment. Such a method may be for monitoring recovery of an individual or managing the treatment of an individual suffering from impending or ongoing cardiovascular disease or, alternatively, may be for monitoring the recovery of an individual, such as an athlete, from strenuous exercise. The individual may be treated or managed according to, for example, the individual's recovery status (such as at least partial, substantial or substantially complete recovery).

A change in the level of modification of said cysteine in the individual's blood is indicative of the individual's recovery. For example, a decrease in the level of modified cysteine in a blood sample from the individual compared to the level during or just after the cardiovascular oxidative stress event or period is indicative of recovery of the individual from the cardiovascular oxidative stress.

In an embodiment of a method of the invention, the level of modification of said cysteine in the individual is compared to the level of modification of said cysteine in a control individual or control population of individuals. The control individual or control population of individuals may be, for example, selected from individuals not suffering from cardiovascular pathophysiology, individuals with impending or existing heart failure, or rested individuals.

In an embodiment of a method of the invention, the level of modification of the cysteine detected in the individual is compared to the level of modification of said cysteine in the individual at an earlier time point.

The method of the invention may be for assessing the efficacy of an agent for treatment or prevention of cardiovascular oxidative stress in an individual, such as treatment of impending or existing heart failure, or treatment of circulatory oxidative damage resulting from strenuous exercise. Such a method may be conducted, for example, as part of a research trial or clinical trial of a candidate agent for the treatment or prevention of cardiovascular oxidative damage.

The method may comprise administering the agent to an individual having cardiovascular oxidative stress and detecting the level of a modified cysteine at position 45 of the β1-subunit of the human erythrocyte ATP-dependent Na$^+$K$^+$ pump protein or of an equivalent cysteine in a homologue or variant thereof in a blood sample from the individual and comparing the detected level of modified cysteine to a standard level indicative of heart failure, or comparing the detected level of modified cysteine to a level of modified cysteine detected for the individual at an earlier time point.

According to an embodiment, the detected level of modified cysteine may be compared to a level of modified cysteine detected for a blood sample obtained from the individual prior to administration of the agent.

A decrease in the level of modified cysteine in a blood sample from the individual after administration of the agent compared to the level prior to the administration may be indicative of an agent capable of treating impending or existing heart failure.

The methods of the invention also permit a clinician to monitor the progress of an individual having ongoing CVD. This allows the clinician to monitor an individual for possible deterioration from a relatively minor clinical risk to a higher clinical risk or to monitor the improvement of an individual from a higher to a lower clinical risk.

Typically this type of monitoring would be done, in the methods of the invention, by detecting the level of modification of eβ1 C45, such as the level of eβ1-GSS in a first blood sample from the individual and detecting the level of modification of eβ1 C45 in a second blood sample from the individual, where the first and second samples have been obtained from the individual at different times. For example, the first may have been obtained prior to treatment being commenced or at the time of, or shortly after an event or period resulting in cardiovascular oxidative stress, and the second may have been obtained after a given period of time during which the individual was undergoing treatment or observation.

Any number of subsequent samples may of course be used in order to further monitor the individual, as may be desirable. Samples may be obtained from the individual at appropriate intervals, such as intervals of one or several hours, or daily or weekly. Samples may be obtained after a certain treatment has been undertaken, such as the administration of a therapeutic agent to treat the CVD or a symptom thereof.

In this manner an increase in the level of modification of β1 C45, such as the level of eβ1-GSS in the second (or subsequent) blood sample compared to said first blood sample is indicative of an increased clinical risk of heart failure in said individual, whereas a decrease is indicative of a reduced clinical risk. Depending on the results of such monitoring, the clinician may adjust the treatment of the individual. The method thus assists clinicians in the treatment and management of individuals.

ATP-Dependent Na$^+$K$^+$ Pump Protein

ATP-dependent Na$^+$—K$^+$ pump (or Na$^+$—K$^+$ ATPase) is a transmembrane enzyme that is responsible for the active transport of Na$^+$ out of cells in exchange for extracellular K$^+$ against their respective electrochemical gradients. A key function of the Na$^+$—K$^+$ pump is to generate the gradients required to maintain the resting membrane potential of electrically excitable cells. These gradients have important additional roles in driving the transmembrane transport of other ions and organic compounds, such as calcium and glucose, and in regulating cell volume.

The sodium pump molecule is a heterooligomer composed of alpha (α), beta (β) and gamma (γ) subunits (see FIG. 1A), having the following sequences:

```
alpha (α) subunit human
                                               (SEQ ID NO: 1)
MGKGVGRDKYEPAAVSEQGDKKGKKGKKDRDMDELKKEVSMDDHKLS

LDELHRKYGTDLSRGLTSARAAEILARDGPNALTPPPTTPEWIKFCR

QLFGGFSMLLWIGAILCFLAYSIQAATEEEPQNDNLYLGVVLSAVVI

ITGCFSYYQEAKSSKIMESFKNMVPQQALVIRNGEKMSINAEEVVVG

DLVEVKGGDRIPADLRIISANGCKVDNSSLTGESEPQTRSPDFTNEN

PLETRNIAFFSTNCVEGTARGIVVYTGDRTVMGRIATLASGLEGGQT

PIAAEIEHFIHIITGVAVFLGVSFFILSLILEYTWLEAVIFLIGIIV

ANVPEGLLATVTVCLTLTAKRMARKNCLVKNLEAVETLGSTSTICSD

KTGTLTQNRMTVAHMWFDNQIHEADTTENQSGVSFDKTSATWLALSR

IAGLCNRAVFQANQENLPILKRAVAGDASESALLKCIELCCGSVKEM

RERYAKIVEIPFNSTNKYQLSIHKNPNTSEPQHLLVMKGAPERILDR

CSSILLHGKEQPLDEELKDAFQNAYLELGGLGERVLGFCHLFLPDEQ

FPEGFQFDTDDVNFPIDNLCFVGLISMIDPPRAAVPDAVGKCRSAGI

KVIMVTGDHPITAKAIAKGVGIISEGNETVEDIAARLNIPVSQVNPR

DAKACVVHGSDLKDMTSEQLDDILKYHTEIVFARTSPQQKLIIVEGC

QRQGAIVAVTGDGVNDSPALKKADIGVAMGIAGSDVSKQAADMILLD

DNFASIVTGVEEGRLIFDNLKKSIAYTLTSNIPEITPFLIFIIANIP

LPLGTVTILCIDLGTDMVPAISLAYEQAESDIMKRQPRNPKTDKLVN

ERLISMAYGQIGMIQALGGFFTYFVILAENGFLPIHLLGLRVDWDDR

WINDVEDSYGQQWTYEQRKIVEFTCHTAFFVSIVVVQWADLVICKTR

RNSVFQQGMKNKILIFGLFEETALAAFLSYCPGMGVALRMYPLKPTW

WFCAFPYSLLIFVYDEVRKLIIRRRPGGWVEKETYY
```

-continued beta (β) subunit human
(SEQ ID NO: 2; C45 in bold and underlined)
MARGKAKEEGSWKKFIWNSEKKEFLGRTGGSWFKILLFYVIFYGCLA

GIFIGTIQVMLLTISEFKPTYQDRVAPPGLTQIPQIQKTEISFRPND

PKSYEAYVLNIVRFLEKYKDSAQRDDMIFEDCGDVPSEPKERGDFNH

ERGERKVCRFKLEWLGNCSGLNDETYGYKEGKPCIIIKLNRVLGFKP

KPPKNESLETYPVMKYNPNVLPVQCTGKRDEDKDKVGNVEYFGLGNS

PGFPLQYYPYYGKLLQPKYLQPLLAVQFTNLTMDTEIRIECKAYGEN

IGYSEKDRFQGRFDVKIEVKS gamma (γ) subunit human
(SEQ ID NO: 3)
MTGLSMDGGGSPKGDVDPFYYDYETVRNGGLIFAGLAFIVGLLILLS

RRFRCGGNKKRRQINEDEP

Detection of cardiovascular oxidative stress in non-human mammalian individuals, including companion animals such as dogs or cats, or other animals such as racing horses, will, of course, require detection of modification of an equivalent cysteine in the equivalent homologue, which can be readily identified by sequence alignment. Within human and non-human populations, variants of the $Na^+$—$K^+$ ATPase, including variants of the component β-subunit, such as may arise by mutation and/or natural variation, may also affect the position of C45 and/or binding of binding agents to the β-subunit or fragment/portion thereof, and appropriate selection of agents for detecting modified C45 or equivalents thereof in such variants may be required.

The instant application provides the first description of a correlation between the level of oxidative modification of C45 of the β1 subunit of circulating erythrocyte $Na^+$—$K^+$ ATPase and the severity of ongoing CVD in individuals.

Individuals

Methods of the invention comprise analysis of an individual's sample for the presence and quantification of modification of a cysteine at position 45 of the β1-subunit of the human erythrocyte ATP-dependent $Na^+K^+$ pump protein or of an equivalent cysteine in a non-human homologue. In this manner the level of modification of this cysteine in the sample may be determined, thereby allowing an assessment of clinical risk for the individual, including whether the individual has heart failure or impending heart failure. Similarly, the methods of the invention permit an assessment of an individual for recovery of an individual from strenuous physical exercise.

It will be understood that the use herein of the term "individual" is intended to have broad meaning. The individual is any individual in respect of which the method is performed and includes human and non-human mammals. Non-human mammals of particular interest include companion animals, such as dogs. The individual may be an individual having or suspected of having CVD, including impending or existing heart failure (such as undiagnosed but mild heart failure). The individual may also be an individual undertaking, or having undertaken strenuous physical exercise, such as an athlete, as such exercise results in circulatory oxidative damage. By way of non-limiting example, the individual may be a hospitalised individual, an individual who presents as a hospital outpatient or emergency department, an individual who presents at a doctor's clinic or surgery or medical practice or at any health assessment or health testing facility. The individual may be an individual who is a member of a population presenting with or without one or more symptoms of circulatory oxidative damage or may be an individual suspected of having circulatory oxidative damage, including post-exercise athletes.

Blood Samples

The step of obtaining a blood sample from an individual may be undertaken as part of a consecutive series of steps in the performance of the method of the invention. The step of obtaining a blood sample from an individual may be undertaken as a distinct step or steps separate from one or more remaining steps of the method of the invention, for example separate in time, location or operator. Accordingly, in the performance of the method of the invention obtaining the blood sample may or may not involve extraction of blood from said individual. Performance of the method of the invention may, for example, comprise receiving a blood sample in a container, the blood having previously been extracted from the individual as an exercise separate from the performance of the method of the invention. As a further example, obtaining a blood sample may comprise retrieving from temporary storage a blood sample extracted from the individual as an exercise separate from the performance of the method of the invention. It will be understood that the performance of the method of the invention may thus be conducted entirely ex vivo.

A blood sample obtained from an individual may undergo one or more transformation steps either as part of the working of the invention or as a separate step or series of steps. For example, where a blood sample is obtained from an individual, the sample may be further processed to produce a more convenient form of blood sample that is used in methods of the invention. This may be, for example, processing of the blood to isolate or free from erythrocyte membranes at least the β1 subunit of the $Na^+$—$K^+$ ATPase. Alternatively, or in addition it may simply be the processing of the blood to expose at least the cysteine of the β1 subunit of the $Na^+$—$K^+$ ATPase to enable this to be bound by, or reacted with the means for detecting the modification of the cysteine, and optionally remove components that might interfere with the efficient operation of the methods.

According to an embodiment, the sample is processed to create a fraction that is used in the determination of the level of oxidative modification of C45 of the β1 subunit of circulating erythrocyte $Na^+$—$K^+$ ATPase. Fractionation of the processed sample, such as may comprise lysed erythrocytes, may be carried out by any one of many techniques known in the art such as, for example, centrifugation, electrophoresis, isoelectric focussing, filtration, affinity binding or other binding chemistries, ion exchange chromatography, hydrophobic interaction chromatography, size-exclusion chromatography, and adsorptive/absorptive techniques, or any combination thereof.

According to another embodiment, erythrocytes within the sample are lysed or otherwise processed to expose at least the modification on C45 of the β1 subunit of circulating erythrocyte $Na^+$—$K^+$ ATPase, or equivalent cysteine in a non-human homologue of said ATPase, such that the modification is free to react with or be bound by the detection means.

The β1 subunit may be cleaved to yield fragments or even individual amino acids (including any modified cysteines) using a chemistry, such as proteolytic cleavage, that does not affect the modified or unmodified cysteine, to prepare the sample for analysis, optionally via further modification(s), for any modified cysteines by, for example, HPLC, colorimetric or fluorometric spectrophotometry, mass spectrometry, gas chromatography, or combinations thereof.

Antibodies

The present invention is based, at least in part, on the identification by the inventors that the level of oxidative modification, such as glutathionylation, of C45 of the β1 subunit of circulating erythrocyte Na$^+$—K$^+$ ATPase in an individual correlates with the severity of CVD in that individual.

Contemplated by the methods of the invention are antibodies which are capable of binding specifically the modification of C45 of the β1 subunit of circulating erythrocyte Na$^+$—K$^+$ ATPase. An antibody or antibodies may be used to qualitatively or quantitatively detect and analyse the modification, such as glutathionylation, of C45 of the β1 subunit of circulating erythrocyte Na$^+$—K$^+$ ATPase. Antibody detection and quantitation of additional polypeptides for the purpose of control or standardization of an assay may also be conducted. By "binding specifically" it will be understood that the antibody is capable of binding to the target polypeptide or fragment thereof with a higher affinity than it binds to an unrelated protein. For example, the antibody may bind to the polypeptide or fragment thereof with a binding constant in the range of at least about $10^{-4}$M to about $10^{-10}$M. Preferably the binding constant is at least about $10^{-5}$M, or at least about $10^{-6}$M, more preferably the binding constant of the antibody to the polypeptide or fragment thereof of interest is at least about $10^{-7}$M, at least about $10^{-8}$M, or at least about $10^{-9}$M or more.

The antibodies may exist in a variety of forms, including for example as a whole antibody, or as an antibody fragment, or other immunologically active fragment thereof, such as complementarity determining regions. Similarly, the antibody may exist as an antibody fragment having functional antigen-binding domains, that is, heavy and light chain variable domains. Also, the antibody fragment may exist in a form selected from the group consisting of, but not limited to: Fv, F$_{ab}$, F(ab)$_2$, scFv (single chain Fv), dAb (single domain antibody), chimeric antibodies, bi-specific antibodies, diabodies and triabodies.

An antibody 'fragment' may be produced by modification of a whole antibody or by synthesis of the desired antibody fragment. Methods of generating antibodies, including antibody fragments, are known in the art and include, for example, synthesis by recombinant DNA technology. The skilled addressee will be aware of methods of synthesising antibodies, such as those described in, for example, U.S. Pat. No. 5,296,348 and Ausubel F. M. et al. (Eds) Current Protocols in Molecular Biology (2007), John Wiley and Sons, Inc.

Antibodies may be prepared from discrete regions or fragments of the polypeptide of interest. An antigenic portion of a polypeptide of interest may be of any appropriate length, such as from about 1 to about 15 amino acids. An antigenic portion may comprise at least about 3, 4, 5, 6, 7, 8, 9, 10, 11, 12, 13, 14 or 15 amino acid residues.

In the context of this specification reference to an antibody specific for a fragment of the β1 subunit of circulating erythrocyte Na$^+$—K$^+$ ATPase refers to a fragment that comprises at least the modification to cysteine 45 or an equivalent thereof.

Antibodies may also be directed against the modification to the cysteine per se. As such, an antibody for use in methods of the present invention may be specific for glutathione when bound to cysteine 45 of the β1 subunit of circulating human erythrocyte Na$^+$—K$^+$ ATPase or an equivalent cysteine in a homologue or variant thereof.

Antibodies that specifically bind a modification of C45 of the β1 subunit of circulating erythrocyte Na$^+$—K$^+$ ATPase can be prepared, for example, using a purified β1 subunit of circulating erythrocyte Na$^+$—K$^+$ ATPase, or a fragment thereof, that comprises at least the modification to C45. Any suitable method for purifying proteins as known in the art may be used. For example, a monoclonal antibody, typically containing Fab portions, may be prepared using hybridoma technology described in Harlow and Lane (Eds) Antibodies—A Laboratory Manual, (1988), Cold Spring Harbor Laboratory, N.Y; Coligan, Current Protocols in Immunology (1991); Goding, Monoclonal Antibodies: Principles and Practice (1986) 2nd ed; and Kohler & Milstein, (1975) Nature 256: 495-497. Such techniques include, but are not limited to, antibody preparation by selection of antibodies from libraries of recombinant antibodies in phage or similar vectors, as well as preparation of polyclonal and monoclonal antibodies by immunizing rabbits or mice (see, for example, Huse et al. (1989) Science 246: 1275-1281; Ward et al. (1989) Nature 341: 544-546).

It will also be understood that antibodies of the invention include humanised antibodies, chimeric antibodies and fully human antibodies. An antibody of the invention may be a bi-specific antibody, having binding specificity to more than one antigen or epitope. Methods for the preparation of humanised antibodies, chimeric antibodies, fully human antibodies, and bispecific antibodies are known in the art and include, for example as described in U.S. Pat. No. 6,995,243 issued Feb. 7, 2006 to Garabedian, et al. and entitled "Antibodies that recognize and bind phosphorylated human glucocorticoid receptor and methods of using same".

Generally, a sample potentially comprising a modification of C45 of the β1 subunit of circulating erythrocyte Na$^+$—K$^+$ ATPase can be contacted with an antibody that specifically binds the polypeptide or fragment thereof. Optionally, the antibody can be fixed to a solid support to facilitate washing and subsequent isolation of the complex, prior to contacting the antibody with a sample. Examples of solid supports include, for example, microtitre plates, beads, ticks, or microbeads. Antibodies can also be attached to a Protein/Chip array or a probe substrate as described above.

Detectable labels for the identification of antibodies bound to the polypeptide of interest include, but are not limited to fluorochromes, fluorescent dyes, radiolabels, enzymes such as horse radish peroxidase, alkaline phosphatase and others commonly used in the art, and colorimetric labels including colloidal gold or coloured glass or plastic/latex beads. Alternatively, the marker in the sample can be detected using an indirect assay, wherein, for example, a second, labelled antibody is used to detect bound marker-specific antibody.

Methods for detecting the presence of or measuring the amount of, an antibody-marker complex include, for example, detection of fluorescence, chemiluminescence, luminescence, absorbance, birefringence, transmittance, reflectance, or refractive index such as surface plasmon resonance, ellipsometry, a resonant mirror method, a grating coupler wave guide method or interferometry. Radio frequency methods include multipolar resonance spectroscopy. Electrochemical methods include amperometric and voltammetric methods. Optical methods include imaging methods and non-imaging methods and microscopy.

Useful assays for detecting the presence of or measuring the amount of, an antibody-marker complex include, for example, enzyme-linked immunosorbent assay (ELISA), a radioimmune assay (RIA), or a Western blot assay. Such methods are described in, for example, Clinical Immunology (Stites & Terr, eds., 7th ed. 1991); Methods in Cell Biology: Antibodies in Cell Biology, volume 37 (Asai, ed. 1993); and Harlow & Lane, supra.

In a particular embodiment the method of the invention may utilise one or more antibodies known in the art. Antibodies capable of binding to glutathione and to the β1 subunit of cardiac myocyte $Na^+$—$K^+$ ATPase (which has substantially the same sequence and structure as the erythrocyte protein) and fragments thereof are known in the art. For example, glutathione-specific antibodies are available from Virogen Corporation (Watertown, Mass., USA). $Na^+$—$K^+$-ATPase antibody is available from Millipore Corporation (Billerica, Mass., USA).

As noted herein, investigation of oxidation of the cardiac myocyte $Na^+$—$K^+$ ATPase (including glutathionylation of C46) by immunoassay has been reported previously (Figtree, G. et at (2009), "Reversible Oxidative Modification: A Key Mechanism of $Na^+$—$K^+$ Pump Regulation", *Circulation Res.* 105: 185-193) the contents of which are incorporated herein by reference. The present invention is based on the unexpected identification by the present inventors that modification of the cysteine at position 45 of circulating erythrocyte β1 subunit correlates with severity of cardiovascular oxidative stress, and severity of cardiovascular disease. Nonetheless, it will be appreciated that the methods, reagents, devices and kits of the present invention may incorporate the use of antibodies previously reported for the investigation of oxidation of the cardiac myocyte $Na^+$—$K^+$ ATPase. It will be appreciated that the invention and therefore the methods, reagents, devices and kits of the invention include any suitable antibody according to the description herein, and is not limited only to those antibodies specifically mentioned herein. The skilled addressee will be aware that suitable antibodies may be identified through literature searches, routine testing and may be listed in online databases, such as www.antibodies-online.com.

Methods and Kits for Detection

As used herein, detecting the level of a modification of C45, such as glutathionylation, of the β1 subunit of circulating erythrocyte $Na^+$—$K^+$ ATPase may in various embodiments include detecting the presence, absence, or amount of said modification in a sample, and may include quantifying the amount of said modification in a sample. In preferred embodiments all steps of the method of the invention occur outside the subject body, such as a subject human body or animal body, such that the method is not practiced on the body. As such, in preferred embodiments the invention does not involve any physical intervention practiced on the human or animal body.

Detecting the level of the modification of C45 of the β1 subunit of circulating erythrocyte $Na^+$—$K^+$ ATPase may include relative quantification, such as where a given sample is assessed for the presence of a eβ1-GSS by comparison to another sample or reference, for example where the test sample is found to comprise more than, less than or about the same amount of cysteine modification as the reference.

Quantifying, and hence determining the level may also include normalization of the sample or the method to account for differences within the assay specific to the sample. This may include determining the level of another component detectable in the sample. For example, samples may be normalized to account for inter-sample differences in performance of the invention. The internal reference marker may be any appropriate component in the sample, such as a gene product and would typically be a component the presence of which is uniform in samples from healthy subjects and in unhealthy subjects, or a component the presence of which is uniform in samples from control or comparative subjects. As a specific example, glyceraldehyde 3-phosphate dehydrogenase (GAPDH) may be used as an internal reference.

Thus the methods of the invention include comparison of the level of the modification of C45 of the β1 subunit of circulating erythrocyte $Na^+$—$K^+$ ATPase in a blood sample from the individual to a reference standard indicative of clinical risk. Any appropriate reference standard may be used. For example the reference standard may be a sample from a healthy subject(s) or may be an amount of the modification typical of that found in a healthy individual(s). In this case an elevated level of modification of C45 in the individual sample compared to the standard is indicative of elevated clinical risk of heart failure in the individual. As a further example the reference standard may be a sample from a rested individual (as compared to an individual during or just after strenuous exercise) or may be a sample from individual(s) with varying degrees of circulatory oxidative damage, including individual(s) with heart failure or individual(s) with mild heart failure.

As a further example the reference standard may be a standard curve defining clinical risk of heart failure from mild to severe. In this case, the reference standard may be independent of the determination of the level of the cysteine modification in the individual sample, for example the standard curve may be in the form of a supplied reference curve defining clinical risk from mild to severe.

The reference standard indicative of clinical risk may be prepared at the same time as determining the level of modification of C45 of the β1 subunit of circulating erythrocyte $Na^+$—$K^+$ ATPase in the blood sample from the individual. For example, this may comprise the preparation of the standard by subjecting one or more known sample(s) of erythrocytes (from individuals of known circulatory oxidative damage) to the same methods for determining levels of oxidative damage as the sample from said individual, wherein the one or more known sample(s) of erythrocytes are of a pre-determined amount or amounts indicative of clinical risk.

As illustrated in specific embodiments of the invention herein, and particularly in the examples, where quantitative detection of eβ1-GSS was undertaken, there was an approximate 2-fold increase in the detected eβ1-GSS in a rabbit infarct model, as compared to the control, and an approximately 3-fold increase in the detected eβ1-GSS in samples from hospitalized heart failure individuals as compared to healthy controls.

Determining the level of modification of C45 of the β1 subunit of circulating erythrocyte $Na^+$—$K^+$ ATPase in a blood sample may also include absolute quantification such as where the amount of C45 modification in a sample is determined such as may be expressed in appropriate units, for example an amount may be expressed as fold change, units/volume of sample, such as grams, micrograms, nanograms, picograms, femtograms, and the like, per milliliter, microliter, nanoliter and the like.

A cut-off value may be implemented in a variety of embodiments of the invention. For example, in one embodiment a cut-off value may be implemented by quantitative measurement of an actual amount of modification of C45 of the β1 subunit of circulating erythrocyte $Na^+$—$K^+$ ATPase in a sample, such as measurement in terms of amount/ml of sample. In another embodiment a cut-off value may be implemented by setting a lower limit or threshold of detectability at the desired cut-off value. In this manner detection of modification of C45 of the β1 subunit of circulating erythrocyte $Na^+$—$K^+$ ATPase in a sample (which, in this context, may be referred to as a positive signal) is indicative of significant risk of heart failure in the individual providing the sample whilst no detectable modification in a sample (which in this context may be referred to as a negative signal) is indicative of the subject providing the sample having mild or no risk of heart failure. Such an embodiment, at any suitable positive/negative cut-off value may find particular use in situations where a relatively rapid diagnosis is desirable or where relatively sophisticated testing equipment is not always available. This may be, for example, at point of care or in a medical practitioner's consulting rooms.

Detection of modification of C45 of the β1 subunit of circulating erythrocyte $Na^+$—$K^+$ ATPase, or of an equivalent cysteine in a non-human homologue, in a sample may be performed using any suitable method. For example, suitable methods may include antibody-based assays such as ELISA and flow cytometry, and fluorescent microscopy. Methods by which the cysteine modifications referred to herein may be identified are generally known in the art, and are described for example in Coligan J. E. et al. (Eds) *Current Protocols in Protein Science* (2007), John Wiley and Sons, Inc; Walker, J. M., (Ed) (1988) *New Protein Techniques: Methods in Molecular Biology*, Humana Press, Clifton, N.J; and Scopes, R. K. (1987) *Protein Purification: Principles and Practice,* 3rd. Ed., Springer-Verlag, New York, N.Y. For example, cysteine modification in the erythrocyte β1 subunit may be detected by western blot or spectrophotometric analysis. Other examples of suitable methods for the detection of polypeptides are described, for example, in U.S. Pat. No. 4,683,195, U.S. Pat. No. 6,228,578, U.S. Pat. No. 7,282,355, U.S. Pat. No. 7,348,147 and PCT publication No. W0/2007/056723.

The method may include detection of whole proteins, peptides or fragments thereof. The method may also further comprise the inclusion of controls, such as for the correct or consistent performance of the method or to permit cysteine modification levels to be normalised between samples. For example, the method may include the detection of one or more polypeptides, or fragment or variant thereof, known to be expressed constitutively, such as GAPDH, or known to be expressed at a consistent level in control or comparative subjects.

Suitable methods for the preparation of samples for detection and/or analysis of the level of the cysteine modifications referred to herein are known in the art, and include, for example, one or more of cell lysis, centrifugation including density gradient centrifugation, permeabilisation, filtration, typically a combination thereof.

Glutathionylation of proteins/peptides may be detected by a number of means including, for example, antibodies directed against glutathione, in situ labelling of reduced thiol groups (after blocking of existing free thiol groups) with biotin using, for example, kits available from Cayman Chemical Company, Ann Arbor, Mich., USA) followed by flow cytometry, binding of glutathione S-transferase, enzymic deglutathionylation of the protein/peptide by glutathione reductases, thioredoxins or disulphide isomerases. Presence of other glutathionylated proteins/peptides in the sample, such as may occur in relatively crude samples, may interfere significantly with non antibody-based detection methods, and therefore more fractionation of the sample(s) may be desirable if using such methods.

Other methods for detection of modification of C45 of the β1 subunit of circulating erythrocyte $Na^+$—$K^+$ ATPase, or of an equivalent cysteine in a non-human homologue, in a sample may comprise fragmentation or proteolytic degradation of the β1 subunit to yield fragments or even individual amino acids (including any modified cysteines) using a chemistry that does not affect the modified or unmodified cysteine, optionally further fractionation to at least partially purify any modified cysteines, followed by analysis of said fragments by any suitable means, such as HPLC, colorimetric or fluorometric spectrophotometry, mass spectrometry, gas chromatography, or combinations thereof.

The methods and kits of the invention especially encompass the use of antibodies, which are capable of binding specifically to at least the cysteine modifications referred to herein, such as glutathionylation. The antibodies may be used to qualitatively or quantitatively detect and analyse one or more polypeptides in a given sample. Methods for the generation and use of antibodies are generally known in the art and described in, for example, Harlow and Lane (Eds) *Antibodies—A Laboratory Manual*, (1988), Cold Spring Harbor Laboratory, N.Y: Coligan, *Current Protocols in Immunology* (1991); Goding, *Monoclonal Antibodies: Principles and Practice* (1986) 2nd ed; and Kohler & Milstein, (1975) Nature 256: 495-497. The antibodies may be conjugated to a fluorochrome allowing detection, for example, by flow cytometry, immunohistochemistry or other means known in the art. Alternatively, the antibody may be bound to a substrate allowing colorimetric or chemiluminescent detection. The invention also contemplates the use of secondary antibodies capable of binding to one or more antibodies capable of binding specifically to the polypeptides of the invention.

According to an embodiment, the methods of the invention comprise contacting said sample with a first binding agent, such as an antibody, which binds specifically to at least the cysteine modification referred to herein, such as a glutathione moiety, and with a second binding agent, such as an antibody, which is specific for said $β_1$ subunit or at least a fragment thereof, which subunit or fragment comprises said modified cysteine. The first binding agent or said second binding agent may be bound to a solid surface. The binding agent not bound to the solid surface may be conjugated to, or conjugatable to a detectable moiety (through, for example, a biotin/avidin binding pair), such as horseradish peroxidase, a radionuclide, a detectable microparticle such as latex particles or other suitable means as known in the art.

In the methods of the invention it will be understood that the description of the use of a sample or preparation, for example, includes the use of less than the total amount available as may determined by the skilled addressee as appropriate in the circumstances. For example, the entire blood sample need not be used if the skilled addressee deems appropriate, an aliquot of the sample may instead be used.

Kits

The invention also provides kits for determining the level of modification of C45 of the β1 subunit of circulating erythrocyte $Na^+$—$K^+$ ATPase, or of an equivalent cysteine in a non-human homologue in a blood sample, the kit comprising at least one agent for detecting the presence of said modification. Any suitable agent capable of detecting cysteine modifications described herein may be included in the kit. According to an embodiment, the kit comprises at least a binding agent specific for said modification and, in a further embodiment, the kit comprises a glutathione-specific binding agent, which may be an antibody or glutathione-S-transferase.

The kit may comprise multiple agents capable of detecting the presence of said cysteine modification in a blood sample, such as have already been discussed above.

According to an embodiment, the kit comprises at least a first binding agent, such as an antibody, which binds specifically to at least the cysteine modification referred to herein, such as a glutathione moiety. In a further embodiment, the kit also comprises at least a second binding agent, such as an antibody, which is specific for at least a fragment of said $\beta_1$ subunit, which fragment comprises said modified cysteine. Alternatively, the kit may comprise a first binding agent, such as an antibody, capable of selectively binding to the cysteine modification, and a second binding agent, such as an antibody, that specifically binds said first binding agent. Where two binding agents are included in the kit, either said first binding agent or said second binding agent may be bound to a solid support and the other binding agent may be conjugated to, or conjugatable to a detectable moiety (through, for example, a biotin/avidin binding pair), such as horseradish peroxidase, a radionuclide, a detectable microparticle such as latex particles or other suitable means as known in the art.

The kit may comprise one or more agents for normalisation of the method of the invention. The agent(s) for normalisation may be selected from the group consisting of an agent for the detection of a constitutively expressed gene product, such as GAPDH.

The kit may comprise one or more calibrated standards wherein the standard comprises a known level of modified cysteine.

The kit may comprise one or more additional components selected from the group consisting of (i) one or more reference sample(s); (ii) one or more detectable moieties; (iii) one or more substance(s) for immobilising an agent for detecting a modification of C45 of the $\beta 1$ subunit of circulating erythrocyte $Na^+$—$K^+$ ATPase, or of an equivalent cysteine in a non-human homologue, on a solid support; (iv) a solid support material; (v) one or more container(s) for collection and/or storage of a blood sample; (vi) one or more reagent(s) for use in preparation of a blood sample; (vii) one or more agents for the amplification of a nucleic acid sequence; and (viii) instructions for use of the kit or a component(s) thereof in a method for determining the level of modification of the C45 of the $\beta 1$ subunit of circulating erythrocyte $Na^+$—$K^+$ ATPase, or of an equivalent cysteine in a non-human homologue in a blood sample.

In general, the kits of the invention may comprise any number of additional components.

By way of non-limiting examples the additional components may include, reagents for cell culture, reference samples, lysis reagent, buffers, labels, and written instructions for performing the detection assay.

According to an embodiment, a kit of the present invention comprise at least:
 a first antibody specific for glutathione when bound to a protein or peptide;
 a second antibody specific for at least a fragment of the $\beta 1$ subunit of circulating erythrocyte $Na^+$—$K^+$ ATPase, wherein said fragment comprises cysteine 45 of said subunit, or of an equivalent cysteine in a non-human homologue;
 reagents for treating a sample in preparation for detection of any modifications to said cysteine, including lysis buffers and reagents, and reaction buffers; and
 instructions for use of the kit or a component(s) thereof in a method for determining the level of modification of C45 of the $\beta 1$ subunit of circulating erythrocyte $Na^+$—$K^+$ ATPase, or of an equivalent cysteine in a non-human homologue in a blood sample;

wherein either said first antibody or said second antibody is bound to a solid support, and the other antibody is conjugated to, or conjugatable to a detectable moiety (through, for example, a biotin/avidin binding pair), such as horseradish peroxidase, a radionuclide, a detectable microparticle such as latex particles or other suitable means as known in the art.

EXAMPLES

The invention will now be described with reference to specific examples, which should not be construed as in any way limiting the scope of the invention.

Example 1

Oxidation of Cysteine 45 of the $\beta 1$ Subunit Results in Inhibition of the ATP-Dependent $Na^+$—$K^+$ Pump FIG. 1A shows the structure of pig kidney $Na^+$—$K^+$-ATPase showing the position of the $\beta 1$ subunit C45 (red circle). α-, β- and γ (a.k.a. FXYD2) subunits are shown as blue, wheat and red. A schematic illustration of mixed disulphide bond between glutathione and reactive cysteine on candidate protein is shown. FIG. 1B illustrates results that show that mutation of the $\beta 1$ subunit Cys45 to tryptophan (α1β1CW) abolishes $ONOO^-$-induced glutathionylation (circle) and inhibition (arrow) of the $Na^+$—$K^+$ pump in Xenopus oocytes.

To identify the nature of the $Na^+$—$K^+$ ATPase residue modified as a result of oxidative stress, Xenopus oocytes were injected with cRNAs encoding the α1 or β1 subunits of $Na^+$—$K^+$ ATPase. cRNAs coding for α1 (10 ng) and wild type β1 (1 ng) or β1C46W mutant (2 ng) were introduced into Xenopus oocytes. After two days of expression, oocytes were injected with biotinylated GSH ester and incubated for 45 min at 19° C. Since in Xenopus oocytes, the basal GSH level was estimated at 2.5 mmol/L and could compete with exogenous biotinylated GSH, 50 nl/oocyte of 25 mmol/L biotinylated GSH ester were injected to achieve a final concentration of 2.5 mmol/L, assuming an intracellular water space of 0.5 µl/oocyte. S-glutathionylation was then activated by injection of oocytes with 50 nl/oocyte of 1 mmol/L peroxynitrite at pH 7.4.

In view of the short half-life of peroxynitrite at pH 7.4, fresh peroxynitrite solutions were prepared from stock solutions after injection of each batch of 40 oocytes. Stock solutions were diluted in MBS (Modified Earth's solution) buffer to a final concentration of 1 mM containing a volume of HCl determined in preliminary experiments to buffer the solution at pH 7.4. The final ionic strength of the MBS buffer is 183 mmol/l for control solution, and 193 mmol/l for ONOO-containing solution. The control oocyte population was either injected with decomposed peroxynitrite stored for 7 months, or was not injected with peroxynitrite. After 15 min incubation at 19° C., oocyte microsomes were prepared with buffers containing 10 mmol/L N-ethylmaleimide. The protein content was determined by the method of Lowry. Microsomal proteins (10 µg) were directly subjected to SDS-PAGE or first pulled down with Streptavidin-Sepharose beads (200 µg), and then transferred overnight at 40 V to nitrocellulose membranes. Membranes were blocked with 10% nonfat dried milk in Tris-buffered saline containing 0.1% Tween-20 and incubated with Xenopus β1 primary antibody (1/1000) and peroxidase coupled secondary antibodies (1/10,000, Amersham Biosciences), and the complex was revealed with the ECL chemiluminescence kit (Amersham Biosciences) according to the manufacturer's protocol.

Example 2

ELISA Assay for Detection of Erythrocyte $\beta_1$-GSS

An ELISA assay has been developed to rapidly and accurately quantify erythrocyte β1 subunit glutathionylation ($e\beta_1$-GSS). Erythrocyte membrane lysates were added to 96-well plates preincubated with, and comprising GSH antibody attached to the well walls. After washing, biotin tagged-$\beta_1$ subunit antibody was added, followed by streptavidin-HRP. After a final washing step, the plate was incubated with equal amount of $H_2O_2$ and tetramethylbenzidine for 20 minutes at room temperature, the reaction stopped with 50 µl of 2N $H_2SO_4$ added to each well and absorbance measured at 450 nm.

The assay is able to measure the degree of glutathionylation (a reversible oxidative modification) of the $Na^+$—$K^+$ pump's β1 subunit, that is causally related to pump inhibition (FIG. 1). It measures this in red cells (erythrocytes), but our experiments show that this reflects very closely what is happening in the heart tissue and in the vasculature Inhibition of the $Na^+$—$K^+$ pump at these sites plays an important part in the pathophysiology of CVD, mediating oxidative changes to cell and organ function.

The assay itself works by utilizing standard ELISA assay concepts, but utilises antibodies specific for eβ1 with a modified C45, or parts thereof bearing said modified cyseine, and/or combinations of such antibodies. The degree of glutathionylation of the erythrocyte's $Na^+$—$K^+$ pump (eβ1-GSS) reflects oxidative stress.

Example 3

Figure 2:
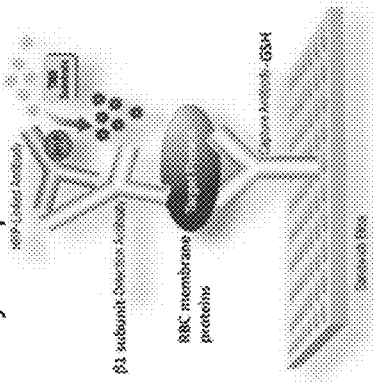
FIG. 2: Shows that the erythrocyte $Na^+$—$K^+$ pump's $\beta1$ subunit was readily detectable by standard western blot technique in rabbits, and was found to be glutathionylated ($e\beta1$-GSS) under conditions of oxidative stress using a GSH antibody and IP (FIG. 2A); illustrates an ELISA assay for reproducible quantification of $e\beta1$-GSS by a method according to the present invention (FIG. 2B); and shows that, in a rabbit infarct model of HF, $e\beta1$-GSS was substantially elevated compared with control (FIG. 2C) and correlated with the oxidative Na—K pump inhibition in cardiac myocytes (FIG. 2D), as well as BNP.
Figure 2:
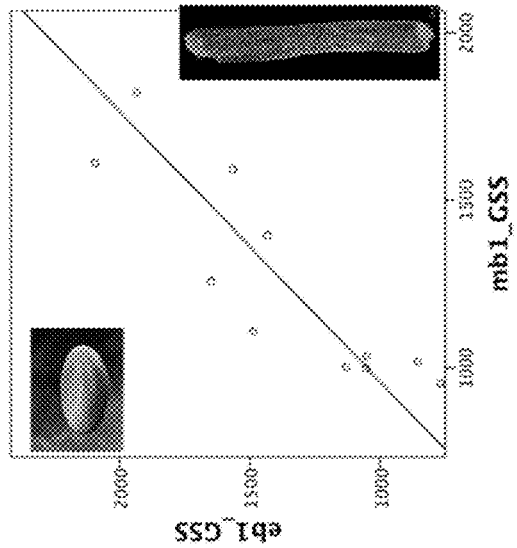
Figure 2:
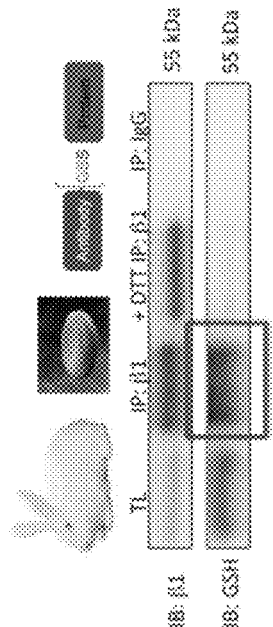
Figure 2:
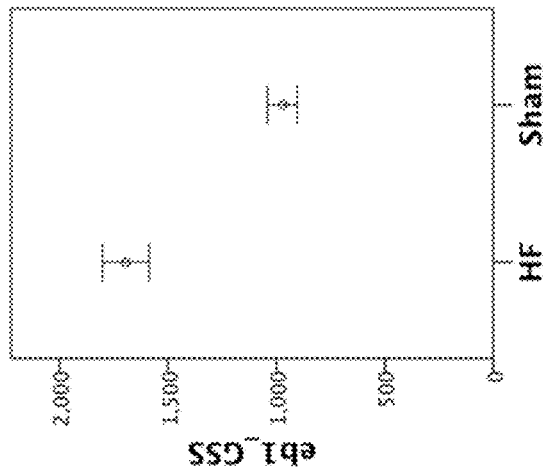
Figure 3:
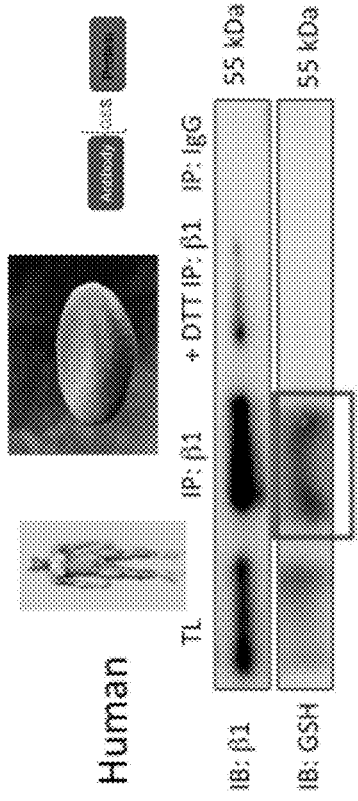
FIG. 3: Shows that the $Na^+$—$K^+$ pump's $\beta1$ subunit was also readily detected in human erythrocytes, and found to be glutathionylated (FIG. 3A). In hospitalized HF individuals $e\beta1$-GSS was significantly higher than healthy controls (FIG. 3B) in association with a ~50% reduction in erythrocyte Na—K pump activity (FIG. 3C).
Figure 3:
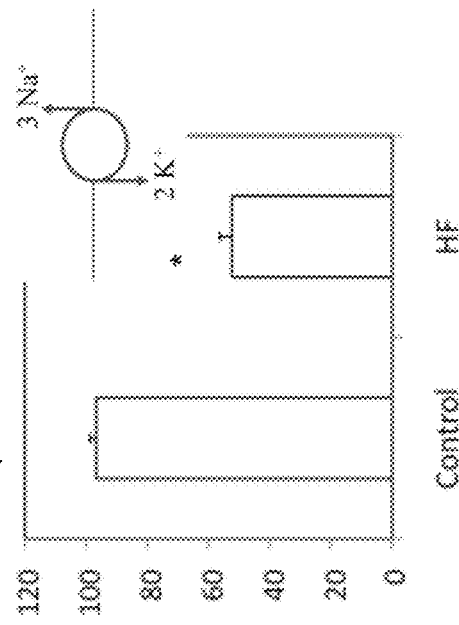
Figure 3:
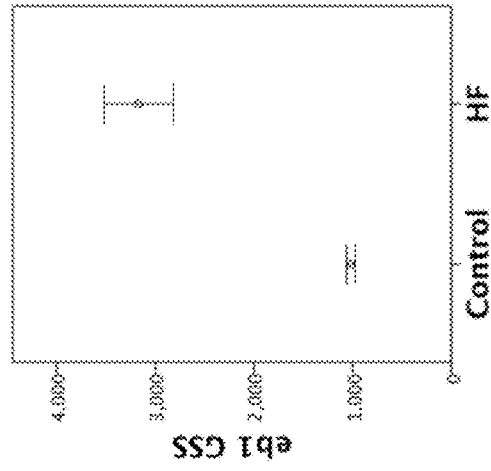
Figure 4:
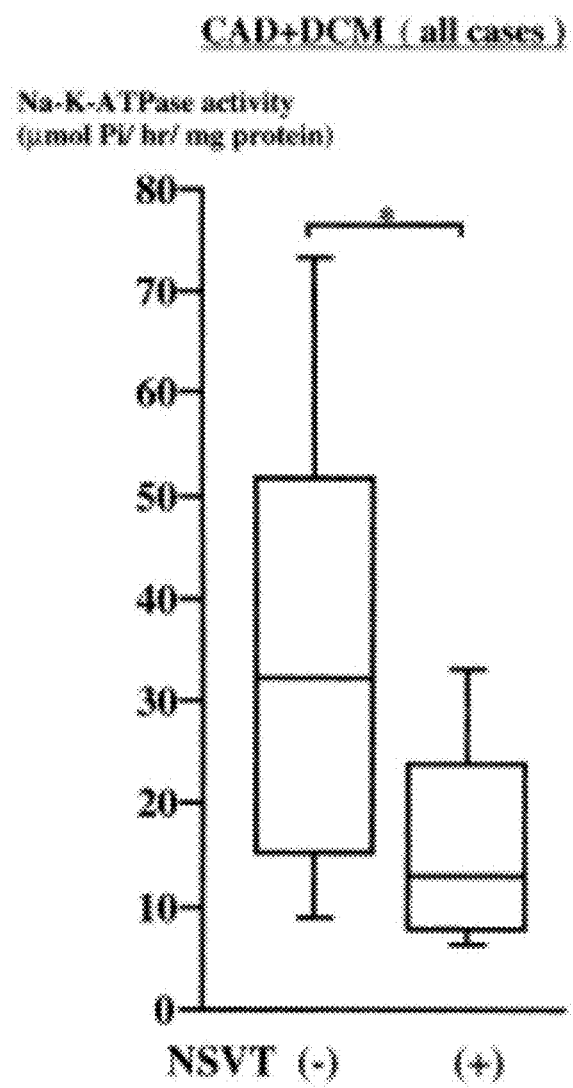
FIG. 4: Shows $Na^+$—$K^+$ ATPase activity (mmol Pi/hr/mg protein) in the presence or absence of VT.

$e\beta_1$-GSS Levels Mirror $m\beta_1$-GSS and Correlate with Severity of Heart Disease The method has been tested in animal models (see FIG. 2) and small human cohorts of heart failure and diabetes (see FIGS. 3 and 4). These tests have confirmed the relationship of eβ1-GSS to severity of heart failure, and to the presence of cardiovascular risk factors.

Rabbit heart failure model: Myocardial infarction was induced in male White New Zealand rabbits via a thoracotomy under anaesthesia, with incision of the pericardium and ligation of the left circumflex coronary artery. Ischaemia was verified by observing for cyanosis in the area at risk and ST segment elevation on the electrocardiogram, and by intraoperative echocardiography. This technique was associated with the development of heart failure from 5-7 days after myocardial infarction, with left ventricular ejection fraction of approximately ~18%. Mortality rate in this model is <20%.

Human heart failure population: blood from 16 hospitalized heart failure patients and 16 healthy control subjects was collected. Indicators of heart failure severity were obtained from the clinical notes, including left ventricular volumes and function, as well as NT-proBNP. Covariates including renal failure, diabetes mellitus, age, gender, body mass index and medication were also recorded.

Preparation of erythrocyte membranes and immunoblotting: erythrocyte membranes were prepared as described by Sachs et al. (Sachs J R, Ellory J C, Kropp D L, Dunham P B, Hoffman J F. (1974), "*Antibody-induced alterations in the kinetic characteristics of the Na:K pump in goat red blood cells*", J Gen Physiol. 63:389-414). Membranes were then frozen at −20° C. Standard Western blot technique was used to examine $Na^+$—$K^+$ pump subunit expression. To detect glutathionylation of the $Na^+$—$K^+$ pump's $\beta_1$ subunit, $\beta_1$ subunit immunoprecipitate from erythrocyte membranes was immunoblotted with an antibody against glutathionylated protein (anti-GSH antibody; Figtree G A, Liu C C, Bibert S, Hamilton E J, Garcia A, White C N, Chia K K M, Cornelius F, Geering K, Rasmussen H H. (2009), "*Reversible oxidative modification: a key mechanism of $Na^+$—$K^+$ pump regulation*", Circ Res. 105:185-193; White C, Liu C, Garcia A, Hamilton E, Chia K K, Figtree G A, Rasmussen H H. (2010), "*Activation of cAMP-dependent signaling induces oxidative modification of the cardiac $Na^+$—$K^+$ pump and inhibits its activity*", J Biol Chem. 285:13712-13720).

As shown in FIG. 2A, the $Na^+$—$K^+$ pump's β1 subunit was readily detectable by standard western blot technique in rabbit erythrocytes, and was found to be glutathionylated (eβ1-GSS) under conditions of oxidative stress using a GSH antibody and β1 subunit immunoprecipitate (FIG. 2A). Exposure of erythrocyte preparation to DTT abolished the detection of eβ1-GSS by the ELISA technique supporting its specificity for mixed disulfide bond/glutathionylation (data not shown).

As shown in FIG. 2B, in a rabbit infarct model of heart failure, eβ1-GSS was 75% higher than in control (1693±108 versus 972±69; p<0.001; n=6) and correlated with the oxidative $Na^+$—$K^+$ pump inhibition in cardiac myocytes (mβ1-GSS; r=0.851; n=18; p<0.001), as well as BNP (r=0.755; n=18; p<0.001). There was a negative correlation between eβ1-GSS and LV ejection fraction (r=−0.842; n=17; p<0.001).

FIG. 3 shows that the erythrocyte $Na^+$—$K^+$ pump β1 subunit was also detected in human erythrocytes, and found to be glutathionylated (FIG. 3A). In hospitalized heart failure individuals eβ1-GSS was significantly higher than healthy controls (3167±164 U vs 1018±20 U; n=16; p<0.001; FIG. 3B) in association with a ~50% reduction in erythrocyte Na—K pump activity (52.3±4 vs 96.7±2; n=16; p<0.001; FIG. 3C). There was a positive correlation between eβ1-GSS and NT-proBNP.

FIG. 4 shows $Na^+$—$K^+$ ATPase activity (mmol Pi/hr/mg protein) for individuals with dilated cardiomyopathy (DCM) or coronary artery disease (CAD) in the presence or absence of non-sustained ventricular tachycardia (NSVT). Individuals with NSVT had lower erythrocyte membrane $Na^+$—$K^+$ ATPase activities than those without NSVT. ATPase activity was measured by estimating the phosphorus liberated after the incubation of erythrocyte membrane, with and without ouabain in a reaction mixture containing ATP with the co-substrate elements at 37° C. for ~15 min.

Summarising the above results, eβ1-GSS is a circulating marker that reflects a physiologically significant consequence of ROS in the microcirculation. The premise that 01-GSS will have prognostic value in individuals at risk of, or diagnosed with HF is supported by: (i) the close correlation between circulating eβ1-GSS and cardiac β1-GSS; (ii) the direct impact of oxidative $Na^+$—$K^+$ pump inhibition on cardiac myocyte physiology; and (iii) eβ1-GSS's reflection of the oxidative stress and neurohormonal abnormalities of HF. Furthermore, because eβ1-GSS reflects the underlying abnormalities driving cardiac dysfunction, it has potential advantages in detecting early heart failure.

eβ1-GSS is easy to measure with a single blood sample. It is stable, and it is a measure of oxidative stress that reflects that in the heart and blood vessels.

It will be appreciated that, although specific embodiments of the invention have been described herein for the purpose of illustration, various modifications may be made without deviating from the spirit and scope of the invention as defined in the following claims.

The invention claimed is:

1. A method of detecting glutathionylation of β1 subunit of human erythrocyte ATP-dependent Na+K+ pump protein in an individual, said method comprising
   a) obtaining a blood sample from the individual,
   b) contacting erythrocyte membranes prepared from said sample with a first antibody specific for glutathione bound to a cysteine residue at position 45 within SEQ ID NO: 1 of the β1 subunit of the human erythrocyte ATP-dependent Na+K+ pump protein and a second antibody specific for the β1 subunit of the human erythrocyte ATP-dependent Na+K+ pump protein comprising the cysteine residue at position 45 within SEQ ID NO: 1, and
   c) detecting the binding between the first antibody and glutathione bound to a cysteine residue at position 45 within SEQ ID NO: 1 of the β1 subunit of the human erythrocyte ATP-dependent Na+K+ pump protein in the blood sample from the individual and the binding between the second antibody and the β1 subunit of the human erythrocyte ATP-dependent Na+K+ pump protein comprising the cysteine residue at position 45 within SEQ ID NO: 1 in the blood sample from the individual.

2. The method of claim 1, further comprising
   quantifying the level of glutathionylation of the cysteine at position 45 of the β1 subunit of the human erythrocyte ATP-dependent $Na^+K^+$ pump protein detected in the individual's blood,
   comparing the quantified level of glutathionylation of a cysteine at position 45 of the β1 subunit of the human erythrocyte ATP-dependent $Na^+K^+$ pump protein detected in the individual's blood with a control.

3. The method of claim 1, wherein said glutathione bound to a cysteine residue at position 45 within SEQ ID NO: 1 of the β1 subunit of the human erythrocyte ATP-dependent $Na^+K^+$ pump protein is a result of cardiovascular oxidative stress.

4. The method of claim 2, wherein the level of glutathione bound to a cysteine residue at position 45 within SEQ ID NO: 1 of the β1-subunit of the human erythrocyte ATP-dependent Na⁺K⁺ pump protein detected in said individual is compared to a control individual or control population of individuals.

5. The method of claim 4, wherein said control individual or control population of individuals is selected from subjects not suffering from cardiovascular pathophysiology, subjects with impending or existing heart failure, or rested subjects.

6. The method of claim 2, wherein the level of glutathione bound to a cysteine residue at position 45 within SEQ ID NO: 1 of the β1-subunit of the human erythrocyte ATP-dependent Na⁺K⁺ pump protein detected in said individual is compared to the level of glutathione bound to a cysteine residue at position 45 within SEQ ID NO: 1 of the β1 subunit of the human erythrocyte ATP-dependent Na⁺K⁺ pump protein in said individual at an earlier time point.

7. The method of claim 1, wherein the first antibody and/or the second antibody is a conjugated antibody.

8. The method of claim 1, wherein the first antibody and/or the second antibody is a polyclonal antibody.

9. The method of claim 1, wherein the first antibody and/or the second antibody is a monoclonal antibody.

10. The method of claim 1, wherein detecting glutathione bound to a cysteine residue at position 45 within SEQ ID NO: 1 of the β1 subunit of the human erythrocyte ATP-dependent Na⁺K⁺ pump protein is present in the blood sample from the individual is by one or more of Western blot analysis, enzyme-linked immunosorbent assay (ELISA) analysis, HPLC analysis, colorimetric of fluorometric spectrophotometry analysis, mass spectrometry analysis, gas chromatography analysis, and flow cytometry analysis.

* * * * *